United States Patent [19]

Powers

[11] 4,187,351
[45] Feb. 5, 1980

[54] IMViC TEST METHOD

[75] Inventor: Edmund M. Powers, Saxonville, Mass.

[73] Assignee: The United States of America as represented by the secretary of the Army, Washington, D.C.

[21] Appl. No.: 855,101

[22] Filed: Nov. 25, 1977

[51] Int. Cl.$^2$ .................................... C12Q 1/10
[52] U.S. Cl. ............................. 435/38; 435/253
[58] Field of Search ............ 195/103.5 M, 127, 139, 195/140, 99, 100, 101, 102, 103

[56] References Cited

U.S. PATENT DOCUMENTS

| | | | |
|---|---|---|---|
| 3,597,326 | 8/1971 | Liner | 195/139 |
| 3,632,478 | 1/1972 | Fink | 195/139 |
| 3,827,942 | 8/1974 | Janik | 195/100 |
| 3,830,703 | 8/1974 | Beckford | 195/103.5 M |
| 3,832,288 | 8/1974 | Rollender et al. | 195/103.5 M |
| 3,846,247 | 11/1974 | Kronich et al. | 195/103.5 M |
| 3,925,163 | 12/1975 | Cekoric, Jr. et al. | 195/103.5 M |
| 3,960,658 | 6/1976 | Avakian et al. | 195/103.5 M |
| 4,010,078 | 3/1977 | Taylor | 195/103.5 M |

OTHER PUBLICATIONS

Martin Frolisher, Fundamentals of Microbiology, 8th Ed., W. B. Saunders Co., 1968, pp. 41 and 42.
Edwin Lennette et al., Manual of Clinical Microbiology, 2nd Ed., American Society for Microbiology, 1974, pp. 898, 906, 910, 924, 933, 937 and 938.

*Primary Examiner*—Raymond N. Jones
*Assistant Examiner*—Robert J. Warden
*Attorney, Agent, or Firm*—Nathan Edelberg; Robert P. Gibson; Lawrence E. Labadini

[57] ABSTRACT

An improved IMViC test method is disclosed which is suitable for conducting multiple bacterial IMViC tests on solid media. The method comprises (1) obtaining a suitable culture of bacteria by growing the bacteria first in LST broth, then in EC broth and finally on EMB agar; (2) inoculating a test plate containing solid test media for the IMViC tests in separate compartments; (3) incubating said inoculated test plate; and (4) determining the results of the tests. The period of incubation for the IMViC tests has been reduced to 48 hours by this method. A test plate suitable for use with this method is also disclosed.

10 Claims, 1 Drawing Figure

IMViC TEST METHOD

The invention described herein may be manufactured, used and licensed by or for the Government for governmental purposes without the payment to me of any royalties thereon.

BACKGROUND OF THE INVENTION

1. Field of the Invention

The invention relates to a method for conducting bacterial IMViC tests. More particularly, the invention relates to an improved method suitable for conducting multiple bacterial IMViC tests on solid media.

2. Description of the Prior Art

The abbreviations used herein are listed in the following table:

TABLE 1

| | |
|---|---|
| C. diversum or freundii | Citrobacter diversum or freundii |
| E. aerogenes or agglomerans | Enterobacter aerogenes or agglomerans |
| EC or E. coli | Escherichia coli |
| EMB | eosin methylene blue |
| IMViC | indole, methyl red, Voges-Proskauer, citrate |
| K. ozaenae, pneumoniae or rhinoscleromatis | Klebsiella ozaenae, pneumoniae or rhinoscleromatis |
| LST | lauryl sulfate tryptose |

Many isolation methods and identifying tests have been developed to determine the identity of bacterial strains. The isolation methods are designed to take advantage of the different growth requirements of the various families of bacteria. By using specific culture (growth) media, it is possible to obtain a culture of bacteria which has a limited number of bacterial strains. These strains may be differentiated further by using appropriate tests. These tests are formulated to take advantage of the various metabolic requirements and products of the large number of known bacterial strains. Thus, using a specific isolation method and a series of tests it is possible to identify an unknown bacterial culture as a specific genus, species and variety. Four such known identifying tests are the indole, methyl red, Voges-Proskauer and citrate tests which are collectively known as the IMViC tests.

The indole test is used to detect the production of indole by the bacterial sample. A positive (+) result indicates the presence of indole in the test medium and is determined by the development of a dark red color upon the addition of the appropriate reagent to the test medium. The methyl red test determines the acidity or basicity of the medium after prolonged incubation of the bacterial sample. A red color which develops upon addition of methyl red indicator to the medium is indicative of an acidic medium and represents the positive result. The bacterial product of acetyl-methyl-carbinol is detected using the Voges-Proskauer test. The positive result is the production of acetyl-methylcarbinol and is indicated by a red color which develops upon the addition of specific reagents to the medium. The growth of bacteria with citrate as the only carbon source is the basis of the citrate test. Bacterial growth on the citrate agar is a positive result and is also indicated by the change in color of the medium from greeen to deep blue. If these results do not occur, the tests are said to be negative.

The IMViC tests are the most important and useful tests for differentiation of coliforms, i.e. bacteria of the genera Escherichia and Enterobacter, into species and varieties. Furthermore, the IMViC tests are used generally for distinguishing members of the family Enterobacteriacea and as a basis for the primary differentiation of *E. coli* and *Enterobacter aerogenes*. For example, *E. coli* type 1 yields a + + − − result respectively to the IMViC tests whereas *Enterobacter aerogenes* yields a −.− + + result respectively to the IMViC tests. The IMViC tests are also useful for confirming the presence of *E. coli* in foods. See for example Speck, M. L., Compendium of methods for microbiological examination of foods, American Public Health Association, Washington, D.C. (1970).

However, the IMViC tests have a severe shortcoming which limits their usefulness particularly for confirming the presence of *E. coli* in foods. This shortcoming is that the IMViC tests are time consuming and procedurally laborious when conducted as prescribed by standard methods. While the indole test requires an incubation of 24 hours and the Voges-Proskauer test requires 48 hours, the methyl red and citrate tests require a minimum incubation of 96 hours. Furthermore, an additional 4 days is required to obtain a suitable culture of the sample bacteria before the IMViC tests may be performed. This length of time makes it impractical to examine the presence of *E. coli* in foods. The prior art IMViC tests are useful, however, for the testing of coliforms where time is not so critical, e.g. fecal coliform determinations. See for example Speck, M. L. supra and Association of Official Analytical Chemists: Official Methods of Analysis, 11th Ed., Ed. Horwitz, W., Association of Analytical Chemists, Washington, D.C. (1970).

Several methods have been developed which reduce the time of incubation for the methyl red and Voges-Proskauer tests. The Voges-Proskauer test was reduced to only a 6 hour incubation by using a massive inoculum of bacteria in 2.0 ml of test medium and standard test reagents. See for example Coblentz. L. M., *Am. J. Public Health* 33, 815 (1943). The time of incubation required for both the methyl red and Voges-Proskauer tests has been reduced to less than 18 hours by using small volumes of the test media. See for example Benjaminson, M. A., De Guzman, B. C. and Weil, A. J., *J. Bacteriology* 87, 234 (1944) and Barry, A. K. Bernshon, K. L., Adams, A. P., and Thrupp, L. D., *Applied Microbiol.* 20, 866 (1970). It has been proposed to perform the citrate test using a test plate rather than the conventional agar slant. This approach yields a positive test for Enterobacter within 24–48 hours. See *Difco Manual*, 9th Ed., Difco Laboratories, Detroit, Mich. (1953). However, none of these methods have been widely accepted or followed. Even if these methods are being followed, they do not provide a simplified test method in which all of the IMViC test media are solid and thus capable of being in one test plate as well as reducing the time of incubation as is disclosed in the present invention.

Another limitation of the prior art is the requirement of four separate tubes to complete the IMViC tests using the conventional methods. This means the laborious procedure of separately handling, labeling, inoculating and incubating the requisite number of tubes. Four separate tubes were required by the prior art since a combination of liquid and solid test media were used. While the citrate test utilized a solid agar, the indole, methyl red and Voges-Proskauer tests utilized liquid broths. It has been reported that the indole test could also be performed using a solid agar. See Roche Diagnostics, Improved Enterotube, Roche Diagnostics, division Hoffman-La Roche Inc., Nutley, New Jersey (1974). No method has been proposed which would allow the methyl red and Voges-Proskauer tests to be performed using solid test media. Thus, no method has been proposed which would eliminate the necessity of using separate tubes for these specific individual test procedures.

In order to perform the IMViC tests a suitable culture of bacteria must first be obtained. The isolation procedure generally followed by the prior art is as follows. LST broth was inoculated with a sample of bacteria and incubated at 35° C. for 24 hours allowing the bacteria to grow. Next, EC broth was inoculated with a sample of bacteria from the LST culture and incubated at 45.5° C. for 24 hours. Then Levine EMB agar was inoculated with a bacterial sample from the EC culture and incubated at 35° C. for 24 hours. Difco Manual, supra, which contains a description of the composition of the above broths and agars is incorporated herein by reference. An isolated colony was transferred to a nutrient agar slant and incubated at 35° C. for 24 hours. This last step was required to grow a large enough culture of bacteria to inoculate the four separate tubes required for the IMViC tests as described above. Each tube, using the conventional method, required a separate inoculation thus a minimum of four inoculums were required for the IMViC tests. Therefore, a single colony of bacteria from the EMB agar would not suffice.

U.S. Pat. No. 3,205,151 and Roche Diagnostics, supra, describe an inoculation device and method for inoculating several compartments or tubes of test media utilizing only a single inoculum. This consists of a series of tubes containing the solid test media in an end to end arrangement. An inoculating needle extends through the center of tubes. A single inoculum is picked up with needle and the needle is pulled through all of the tubes inoculating each test media. Since only one colony is required for the inoculation, this colony could be obtained from an EMB culture without the need of growing the bacteria in a nutrient agar or broth. However, these references only disclose the use of a single inoculum, and do not disclose using solid methyl red and Voges-Proskauer test medium.

The IMViC test method of this invention yields at least equally reliable and precise results as obtained with the cumbersome and laborious methods of the prior art. For example, using the improved method of this invention *E. coli* type 1 yields the same + + − − result as obtained with the prior art. In addition, the improved method is designed to be performed in a single test plate containing compartmentalized, solid test media, thereby eliminating the need for separate tubes of the media. The improved method is also designed to require substantially less time by reducing the incubation time of the methyl red and citrate tests and by reducing the time necessary to obtain a suitable bacterial culture. Thus, at least as equally reliable and precise results are obtained within 48 hours using the improved IMViC test method of this invention when compared to the methods of the prior art. And in fact, the prior art methods need more time to yield the results which are obtained within 48 hours by this invention.

SUMMARY OF THE INVENTION

The disadvantages of the prior art are obviated by the present invention. The invention has at least the following advantages; the time required to identify *E. coli* is reduced by 72 hours which is accomplished by reducing the steps of growing the bacteria and reducing the incubation time of the IMViC tests; it eliminates the handling, labeling, inoculating and incubating of separate tubes for each test; all media are solid and in a single test plate and thus can be inoculated with a single inoculum from a single colony; all of the test reagents are added to the single test plate which makes the reading of the results more convenient; less space is required for incubating the plates, and by providing solid test media, it is now possible to mass produce an IMViC test plate. The invention yields correct responses for all bacteria examined after only a 48 hour incubation of the inoculated test media.

The improved IMViC test method comprises growing the bacteria first in LST broth, then in EC broth and finally on EMB agar, inoculating a test plate in which all of the test media are solid and compartmentalized with a single inoculum, incubating the test plate for 48 hours and determining the results of the tests.

Figure 1:
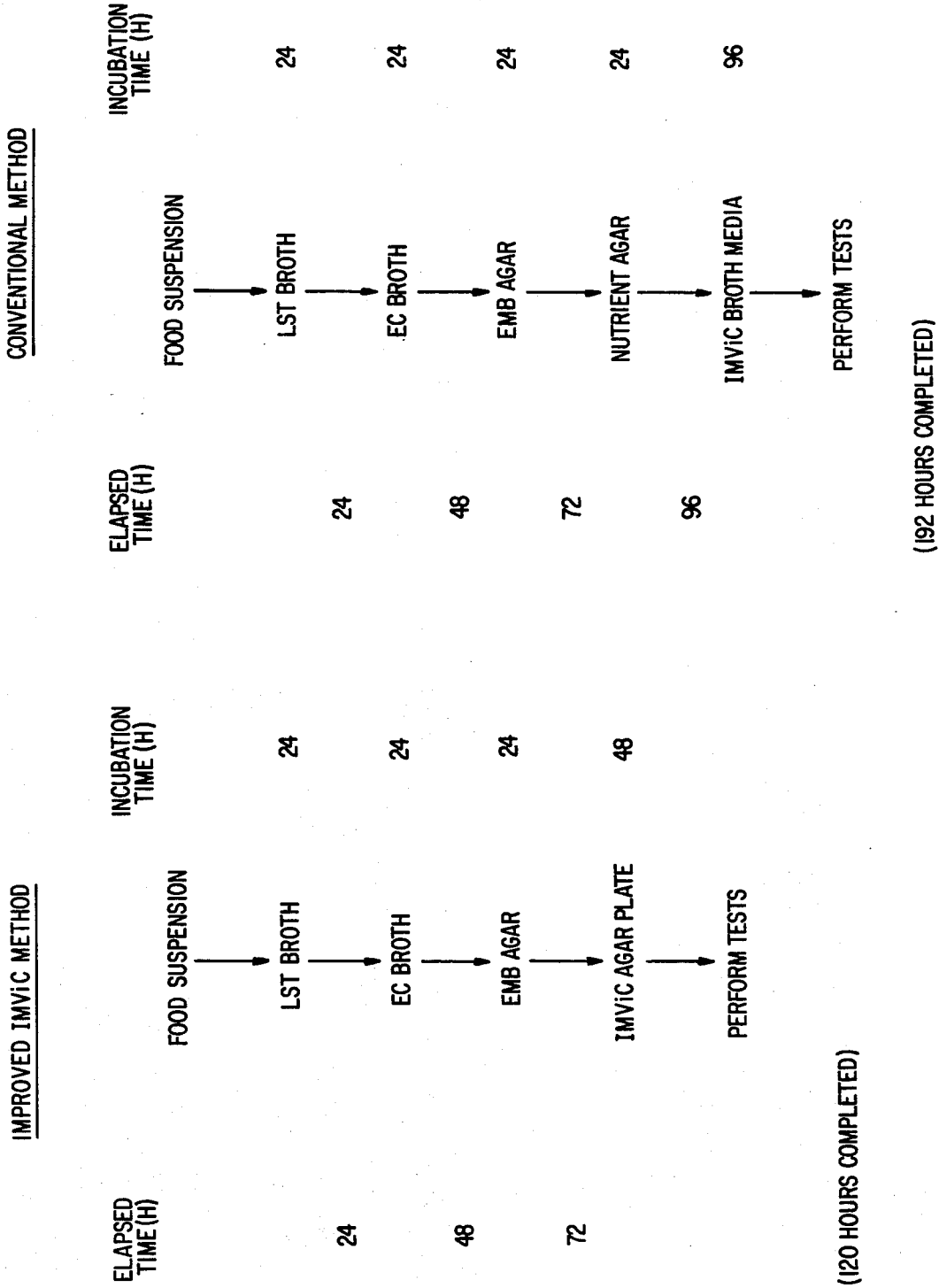
FIG. 1 is a comparison between the flow charts of the prior art or conventional method and the improved method of this invention.

DESCRIPTION OF THE PREFERRED EMBODIMENTS (i) Agar Test Methods

All media were purchased from Difco Laboratories, Detroit, Mich. Difco Manual, supra, which contains a description of their media and Association of Official Analytical Chemists, supra, and Speck, M. L., supra, both of which contain a description of test media and methods are incorporated herein by reference.

The test medium for the indole test consists of a modified tryptophane medium. The modified medium consists of 1.5% tryptone and 1% agar which is, therefore, solid instead of the conventional liquid broth containing only 1% tryptone. The tryptone and 1% agar medium was dissolved by steaming and sterilized at 121° C. for 15 minutes. The modified Kovacs reagent as described by Gadebusch, H. H., *Am. J. Clinical Pathol.* 26, 1373 (1956) was used for the detection of indole. The modified Kovacs reagent consists of 5 g of paradimethlaminobenzaldehyde, 25 ml of concentrated hydrochloric acid and 75 ml of isoamyl alcohol. This reagent must be straw colored in order to function properly. To test for the production of indole, the bacterial growth on the medium surface is flooded with 0.3 ml of the modified Kovacs reagent. If a red color results, indole is present and the test is positive.

The test medium for the methyl red and Voges-Proskauer tests consists of a modified un-buffered glucose peptone medium. The modified medium consists of substituting sodium chloride (NaCl) for dipotassium phosphate as described by Smith, N. R., Gordon, R. E., and Clark, F. E., Agriculture Monograph No. 16, U.S. Government Printing Office, Washington, D.C. (1952) and Speck, M. L., supra, and adding agar to 1% concentration. The composition of the medium per liter of solution was 7 g of proteose peptone, 5 g of glucose, 5 g of NaCl and 10 g of agar. The medium was dissolved by steaming and sterilized at 121° C. for 15 minutes. The pH of the medium was 6.3. The addition of agar yields a solid medium as compared with the conventional liquid broth of the prior art.

The methyl red test was performed by adding 5 drops of methyl red indicator to the bacterial growth on the medium surface. The methyl red indicator was prepared by dissolving 0.1 g of methyl red in 300 ml of 95% ethyl alcohol and diluting to 500 ml with distilled water. A resultant red color is indicative of an acidic medium and represents the positive result. The Voges-Proskauer test was performed by flooding the bacterial growth on the medium surface with 0.6 ml of naphthol reagent followed by 0.2 ml of creatine-potassium hydroxide (KOH) reagent. The naphthol reagent consists of 5% alpha-naphthol in absolute ethyl alcohol. The creatine-KOH reagent consists of 0.3% creatine and 40% KOH. The development of a red color indicates the presence of acetyl-methyl-carbinol and is the positive result.

The citrate test medium consists of the Simmons citrate agar as described in Simmons, J. S., *J. Infectious Disease*, 39, 209 (1926). It consists of 0.2 g of magnesium sulfate, 1 g of monoammonium phosphate, 1 g of dipotassium phosphate, 2 g of sodium citrate, 5 g of sodium chloride, 0.08 g of Brom Thymol Blue and 15 g of agar per liter of solution. The medium was dissolved by steaming and sterilized at 121° C. for 15 minutes. A positive result is indicated by bacterial growth on the medium surface and a change in color of the medium from green to deep blue.

(ii) The Improved IMViC Test Method

Bacteria may be obtained from any source, e.g. foods, clinical samples or laboratory cultures. The bacterial samples may be isolated using conventional methods. See Speck, M. L., supra, and Association of Official Analytical Chemists, supra. The preferred isolation method comprises: (a) inoculating a tube containing LST broth with a sample of bacteria and incubating the inoculated LST broth at 35° C. for 24 hours to allow the bacteria to grow; then, (b) inoculating a tube containing EC broth with a sample of bacteria taken from the LST culture and incubating the inoculated EC broth at 45.5° C. for 24 hours to allow the bacteria to grow; and finally, (c) inoculating a plate containing Levine EMB agar with a sample of bacteria taken from the EC culture and incubating the inoculated EMB agar at 35° C. for 24 hours to allow the bacteria to grow. A single, well-isolated colony of bacteria from the EMB agar is used to inoculate the IMViC test plate of the present invention.

The test plate is prepared by pouring 4 ml of each of the IMViC test media of the invention into separate compartments of a "X"-compartmented petri dish, i.e. a petri dish having four compartments, and allowing the media to solidify. All four test media are inoculated simultaneously as follows. A single, well-isolated colony is picked from the EMB agar with an inoculating needle in a conventional manner. A single streak is made on the surface of each of the test media in succession without returning to the original colony. The citrate test medium is inoculated first to avoid the introduction of extraneous carbon or nitrogen sources from the other test media. The remaining test media may be inoculated in any order. However, it is more convenient to inoculate the indole test medium second and finally to inoculate the methyl red and Voges-Proskauer test media. The inoculated test plate is incubated at 35° C. for 48 hours. At this time the results of the tests are determined as described above.

The present invention will be more fully described by reference to the following examples which represent a comparison of the present invention with the conventional IMViC test method. The following examples are not intended to limit the invention disclosed except to the extent that limitations appear in the appended claims.

EXAMPLES

In the following examples all incubations were at 35° C. for the period of time indicated. The same test reagents were used in the comparisons of the examples. A + indicates a positive reaction and a − indicates a negative reaction. Several +'s indicate the degree of reaction noted with + + + + being the strongest reaction. A ∓ indicates a reaction which was initially slightly pink, but doubtful after 4 hours.

EXAMPLE 1

This example compares indole test medium containing 1% tryptone and 1.5% tryptone both also containing 1% agar, as described above for five cultures of *E. coli*. The samples were compared after incubation times of 24, 48, 72 and 96 hours at 35° C. The results were determined as described above. Table 2 shows the results obtained in this comparison.

Table 2

| | COMPARISON OF 1% TRYPTONE WITH 1.5% TRYPTONE FOR PRODUCTION OF INDOLE BY *ESCHERICHIA COLI* | | | | | | | |
|---|---|---|---|---|---|---|---|---|
| | INDOLE TEST MEDIUM CONTAINING 1% AGAR AND | | | | | | | |
| | 1% TRYPTONE | | | | 1.5% TRYPTONE | | | |
| CULTURE | 24 h | 48 h | 72 h | 96 h | 24 h | 48 h | 72 h | 96 h |
| *E. coli* (NARADCOM) | +++ | +++ | +++ | +++ | +++ | +++ | ++++ | +++ |
| *E. coli* B2C | +++ | +++ | +++ | +++ | +++ | +++ | ++++ | +++ |
| *E. coli* FDA 4 | +++ | +++ | +++ | − | +++ | +++ | ++++ | + |
| *E. coli* FDA 5 | +++ | +++ | +++ | ∓ | +++ | +++ | +++ | +++ |
| *E. coli* ROCKEFELLER | +++ | +++ | +++ | − | +++ | +++ | +++ | − |

Referring to Table 2, both media yielded identical results for all five varieties through 72 hours of incubation, but the medium containing 1.5% tryptone was more sensitive at 96 hours. Since the 1.5% tryptone medium was slightly more sensitive than the 1% tryptone medium when all conditions were constant, the 1.5% tryptone medium was selected as the preferred medium as a precaution to insure against inadvertent false results thereby obtaining the best results. For this reason, the 1.5% tryptone medium is preferred even though the 1% tryptone medium is probably adequate.

EXAMPLE 2

This example compares the modified unbuffered glucose peptone medium of the present invention with the buffered glucose peptone medium (see, Difco Manual, supra) of the prior art to which 1% agar has been added.

The results were determined as described above for both the methyl red and Voges-Proskauer tests after incubations at 35° C. for 24, 48, 72 and 96 hours. Fifteen cultures of bacteria of the family Enterobacteriaceae were used in this comparison. Table 3 illustrates the comparison of the two methods for the methyl red test and Table 4 shows the comparison of the Voges-Proskauer test for both methods.

obtained after 24 hours of incubation and was correct through 72 hours for all of the bacteria examined.

EXAMPLE 3

In comparing the improved IMViC test method of this invention to the method of the prior art, conventional procedures and media were used as described by Speck, M. L. supra, and Association of Analytical Table 3

COMPARISON OF METHYL RED TEST FOR COLIFORMS USING MODIFIED UNBUFFERED GLUCOSE PEPTONE MEDIUM AND BUFFERED GLUCOSE PEPTONE MEDIUM PLUS 1% AGAR

METHYL RED TEST

| Culture | Modified Unbuffered Glucose Peptone Medium | | | | Buffered Glucose Peptone Medium | | | |
|---|---|---|---|---|---|---|---|---|
| | 24h | 48h | 72h | 96h | 24h | 48h | 72h | 96h |
| E. coli FDA 1 | ++++ | ++++ | ++++ | + | − | − | − | − |
| E. coli FDA 2 | ++++ | ++++ | ++++ | ++++ | − | +++ | +++ | +++ |
| E. coli FDA 3 | ++++ | ++++ | ++++ | ++++ | − | + | − | − |
| E. coli FDA 4 | ++++ | ++++ | ++++ | ++++ | − | + | ++ | − |
| E. coli FDA 5 | ++++ | ++++ | +++ | +++ | − | + | − | − |
| E. coli Rockefeller | ++++ | ++++ | ++++ | ++++ | − | + | − | − |
| E. coli ATCC 11840 | ++++ | ++++ | ++++ | ++++ | − | + | − | − |
| E. coli B2C | ++++ | ++++ | ++++ | ++++ | − | − | − | − |
| E. coli NARADCOM | ++++ | ++++ | ++++ | ++++ | − | + | ++ | − |
| E. aerogenes 1 | − | − | − | − | − | − | − | − |
| E. aerogenes 2 | ++ | − | − | − | − | − | − | − |
| Enterobacter 3 | +++ | − | − | − | − | − | − | − |
| K. pneumoniae DMV 2 | +++ | − | − | − | − | − | − | − |
| K. pneumoniae DM591 | +++ | − | − | − | − | − | − | − |
| K. pneumoniae DM602 | +++ | − | − | − | − | − | − | − |
| Uninoculated Medium | − | − | − | − | − | − | − | − |

Table 4

COMPARISON OF VOGES-PROSKAUER TEST FOR COLIFORMS USING MODIFIED UN-BUFFERED BLUCOSE PEPTONE MEDIUM AND BUFFERED GLUCOSE PEPTONE MEDIUM PLUS 1% AGAR

VOGES-PROSKAUER TEST

| Culture | Modified Un-Buffered Glucose Peptone Medium | | | | Buffered Glucose-Peptone Medium | | | |
|---|---|---|---|---|---|---|---|---|
| | 24h | 48h | 72h | 96h | 24h | 48h | 72h | 96h |
| E. coli FDA 1 | − | − | − | − | ∓ | ∓ | ∓ | ∓ |
| E. coli FDA 2 | − | − | − | − | ∓ | ∓ | ∓ | ∓ |
| E. coli FDA 3 | − | − | − | − | ∓ | ∓ | ∓ | ∓ |
| E. coli FDA 4 | − | − | − | − | ∓ | ∓ | ∓ | ∓ |
| E. coli FDA 5 | − | − | − | − | ∓ | ∓ | ∓ | ∓ |
| E. coli Rockefeller | − | − | − | − | ∓ | ∓ | ∓ | ∓ |
| E. coli 11840 | − | − | − | − | ∓ | ∓ | ∓ | ∓ |
| E. coli B2C | − | − | − | − | ∓ | ∓ | ∓ | ∓ |
| E. coli NARADCOM | − | − | − | − | ∓ | ∓ | ∓ | ∓ |
| E. aerogenes 1 | ++++ | ++++ | ++++ | ++++ | +++ | ++++ | ++++ | ++++ |
| E. aerogenes 2 | ++++ | ++++ | ++++ | ++++ | ++++ | +++ | + | +++ |
| Enterobacter 3 | ++++ | ++++ | ++++ | ++++ | ++++ | ++++ | ++++ | ++++ |
| K. pneumoniae DMV2 | ++++ | ++++ | ++++ | ∓ | +++ | − | − | − |
| K. pneumoniae DM591 | ++++ | ++++ | ++ | ++ | + | + | − | − |
| K. pneumoniae DM602 | ++++ | ++++ | +++ | ++ | + | − | − | − |
| Uninoculated Medium | No Reaction | | | | No Reaction | | | |

Tables 3 and 4 show that the buffered glucose medium with added agar was unsuitable for both the methyl red and Voges-Proskauer tests whereas the modified unbuffered glucose peptone medium of the present invention was suitable. Table 3 shows that 48 hours were required to give typical methyl red responses for all bacteria tested. At 24 hours, five species of Enterobacter and Klebsiella gave false positive methyl red test results which were correct at 48 hours. Table 4 shows that proper responses for the Voges-Proskauer test was Chemists, supra. The conventional tests using liquid media for the indole, methyl red and Voges-Proskauer tests and an agar slant for the citrate test were performed in parallel with the present invention and all test reagents were the same for both methods. However, each conventional tubed medium was inoculated with a separate inoculum. All incubations were at 35° C. for 24 and 48 hours, and longer if required by the conventional method. All results were determined as described above. Eighty-seven cultures of bacteria of the family Enterobacteriaceae were used in this comparison and the results are shown in Table 5.

Table 5
IMViC REACTIONS OF ENTEROBACTERIACAE USING THE IMPROVED IMViC METHOD AND THE CONVENTIONAL METHOD

| | No. of Strains Tested | Typical (correct) IMViC Reactions | Number of Strains Giving Typical Reactions | | | |
|---|---|---|---|---|---|---|
| | | | Improved Method | | Conventional Method[a] | |
| | | | 24h | 48h | 24h | 48h |
| E. coli type 1 | 24 | + + − − | 24 | 24 | 22[b] | 24 |
| E. coli type 2 | 4 | − + − − | 4 | 4 | 4 | 4 |
| Enterobacter sp. | 12 | − − + + | 3[c] | 12 | 4[c] | 8[c,d] |
| E. agglomerans (14/73) | 1 | − + − + | 1 | 1 | 1 | 1 |
| K. pneumoniae (indole −) | 9 | − − + + | 1[c] | 9 | 3[c] | 6[c,d] |
| K. pneumoniae (indole +) | 4 | + − + + | 2[c] | 4 | c | 3[d] |
| K. ozaenae | 2 | − + − − | 2 | 2 | 2 | 2 |
| K. rhinoscleromatis | 2 | − + − − | 2 | 2 | 2 | 2 |
| C. freundii | 3 | − + − + | 3 | 3 | 2[b] | 3 |
| C. diversum | 1 | + + − + | 0 | 1 | 0 | 1 |
| Salmonella sp. | 23 | − + − + | 23 | 23 | 21[e] | 21[e] |
| Proteus sp. | 2 | + + − − | 2 | 2 | 1[b] | 1[b] |

[a]All media were liquid except Simmons Citrate agar slant.
[b]Remainder of cultures gave false negative MR tests in MR-VP broth.
[c]Remainder of cultures gave false positive MR tests.
[d]One culture gave a false negative citrate test in 48 h but was positive after 96 h.
[e]Two cultures gave equivocal MR reactions (orange).

The typical IMViC reactions shown are for the indole, methyl red, Voges-Proskauer and citrate tests respectively. *Klebsiella pneumoniae* indicated as indole + in Table 5 represents *K. pneumoniae* Types I and II, whereas *K. pneumoniae* indicated as indole − represents *K. pneumoniae* Type III. Table 5 shows that the 30 bacterial strains of the Enterobacter species and *Klebsiella pneumonia* yielded slightly better IMViC responses at 24 hours using the conventional method whereas the remaining strains of bacteria yielded slightly better results at 24 hours using the improved method of this invention. However, the improved method yielded typical IMViC responses at 48 hours for all bacterial strains examined whereas the conventional method sometimes required an incubation of 96 hours to give all of the correct responses. The conventional method required additional incubation because of delayed methyl red and citrate reactions. It was also noted that less time was required for the individual reactions to occur once the test reagents were added to the IMViC test plate of this invention as compared with the conventional liquid medium.

CONCLUDING REMARKS

The more rapid methyl red and citrate tests of the present invention are attributed to a larger surface area of the test medium which is exposed to atmospheric oxygen thus resulting in faster growth of the bacterial culture. This has also been indicated by Barry, A. L., et al, supra, and Difco Manual, supra, for the methyl red and citrate tests respectively. Since the methyl red and citrate tests of this invention give correct results after 48 hours of incubation, the improved IMViC test method of this invention requires 48 hours less time for incubation than that required by the prior art.

In the conventional method an additional step was required in the isolation of bacteria from sources other than pure cultures. This step was a 24 hour incubation of a single colony of bacteria from the EMB agar in a nutrient broth. This was necessary to provide enough bacteria of a single colony to inoculate the four separate tubes required for the conventional IMViC method. Thus, since only a single inoculum is required to inoculate the test plate of the present invention, an additional 24 hours can be saved in the overall process by eliminating the nutrient broth culturing step. Therefore, a total savings of 72 hours can be achieved by using the method of this invention. FIG. 1 shows the flow charts for the isolation and identification of the bacteria using the conventional method and the method of this invention. It illustrates the 72 hour time savings which can be accomplished by using this invention. Moreover, the improved IMViC test method as herein disclosed and claimed simplifies the laboratory procedure by eliminating the handling and inoculating of separate tubes, by requiring only a single inoculum to inoculate all four test media, and by being able to add all of the reagents to a single plate and reading the results of the reactions thereon. Furthermore, the present invention yields typical reaction responses for all bacteria examined after only a 48 hour incubation of the IMViC test plate.

An additional advantage of the present invention is that it enables the mass production of a pre-measured test plate. Since all of the IMViC test media are solid as herein disclosed, it is now possible to prepare a test plate containing a pre-measured amount of the test media by mass production on a quality control basis. A pre-measured test plate is advantageous in that it eliminates the time and avoids the messiness associated with preparing and pouring solutions of the test media into a test plate before using the improved IMViC test method herein disclosed and thereby makes the procedure less laborious.

What is claimed is:

1. An improved IMViC test method suitable for confirming the presence of *Escherichia coli*, for differentiating between bacteria of the genera Escherichia and Enterobacter and for distinguishing members of the family Enterobacteriaceae which comprises:
   obtaining a suitable culture of said bacteria;
   inoculating a test plate with an isolated colony of said bacteria from said suitable culture, said test plate containing test media for (a) indole, (b) methyl red, (c) Voges-Proskauer and (d) citrate tests in separate compartments wherein each of said test media is a solid agar medium and wherein the test medium for the methyl red and Voges-Proskauer tests is an unbuffered glucose peptone medium in which sodium chloride is substituted for dipotassium phosphate;

incubating said inoculated test plate to enable said bacteria to grow on said test plate; and, determining the results of said tests.

2. The improved IMViC test method of claim 1 wherein said indole test medium consists of tryptophane medium and wherein said citrate test medium consists of Simmons citrate agar.

3. The improved IMViC test method of claim 2 wherein said unbuffered glucose peptone medium consists of 7 g of proteose peptone, 5 g of glucose, 5 g of NaCl and 10 g of agar per liter of solution.

4. The improved IMViC test method of claim 2 wherein the result of said indole test is determined by flooding said bacterial growth on said indole test medium with modified Kovacs reagent.

5. The improved IMViC test method of claim 4 wherein the result of said methyl red test is determined by adding methyl red indicator to said bacterial growth on said methyl red test medium.

6. The improved IMViC test method of claim 5 wherein the result of said Voges-Proskauer test is determined by flooding said bacterial growth on said Voges-Proskauer test medium with naphthol reagent followed by creatine-KOH reagent.

7. The improved IMViC test method of claim 1 wherein said suitable culture of bacteria is obtained by first growing the bacteria in lauryl sulfate tryptose broth, then in a broth capable of supporting *E. coli* and finally on eosin methylene blue.

8. The improved IMViC test method of claim 7 wherein said test plate is inoculated by picking up said isolated colony of bacteria from said eosin methylene blue agar with an inoculating needle and streaking said bacteria on said test media of said test plate.

9. The improved IMViC test method of claim 8 wherein said streaking is performed on the surface of each of said test media of said test plate in succession beginning with the compartment containing said citrate test medium.

10. The improved IMViC test method of claim 9 wherein the streaking is performed in succession without the need to return to said colony of bacteria.

* * * * *